(12) United States Patent
Edwards et al.

(10) Patent No.: US 8,702,702 B1
(45) Date of Patent: Apr. 22, 2014

(54) SURGICAL CUTTING INSTRUMENT WITH ELECTROMECHANICAL CUTTING

(71) Applicant: Gyrus ACMI, Inc., Southborough, MA (US)

(72) Inventors: Kevin C. Edwards, Olive Branch, MS (US); Phillip A. Ryan, Memphis, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 76 days.

(21) Appl. No.: 13/646,229

(22) Filed: Oct. 5, 2012

(51) Int. Cl.
*A61B 18/18* (2006.01)
(52) U.S. Cl.
USPC .................................. 606/48; 606/52; 606/50
(58) Field of Classification Search
USPC ....................................................... 606/45–52
See application file for complete search history.

(56) References Cited

U.S. PATENT DOCUMENTS

| | | |
|---|---|---|
| 4,646,738 A | 3/1987 | Trott |
| 5,106,364 A | 4/1992 | Hayafuji et al. |
| 5,707,350 A | 1/1998 | Krause et al. |
| 5,904,681 A * | 5/1999 | West, Jr. .......................... 606/41 |
| 6,258,111 B1 | 7/2001 | Ross et al. |
| 7,247,161 B2 | 7/2007 | Johnston et al. |
| 7,318,831 B2 | 1/2008 | Alvarez et al. |
| 2006/0178670 A1 | 8/2006 | Woloszko et al. |

FOREIGN PATENT DOCUMENTS

EP 0 923 907 A1 6/1999

OTHER PUBLICATIONS

Jul. 29, 2013 International Search Report and Written Opinion issued in International Patent Application No. PCT/US2013/039820.

* cited by examiner

*Primary Examiner* — Linda Dvorak
*Assistant Examiner* — Amanda Scott
(74) *Attorney, Agent, or Firm* — Oliff PLC

(57) ABSTRACT

A mechanical cutting device that makes use of mechanical (rotary) motion and suction to engage tissue also applies a cutting energy sufficient to vaporize the tissue. The rotation and suction are used to engage the tissue (sucking tissue into cutting windows when the cutting windows of inner and outer blades are aligned), and then the cutting member(s) function as an electrode(s) by having an electrical cutting signal applied thereto so that the cutting member(s) electrically cut the tissue as the cutting members relatively rotate. The electrical cutting signal is only applied as the windows become aligned up until the cutting of the tissue is completed. The cutting signal preferably is stopped after the cutting windows become misaligned. While the cutting windows are misaligned, a coagulation signal can be supplied to the cutting member so that the device functions as an electrocautery device.

17 Claims, 15 Drawing Sheets

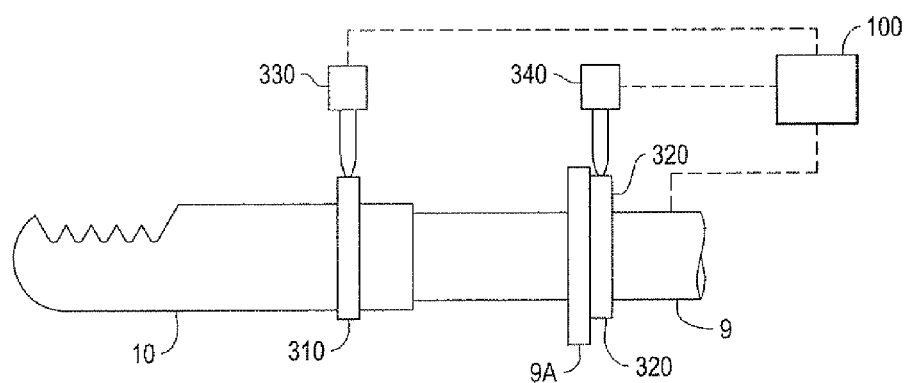
FIG. 14
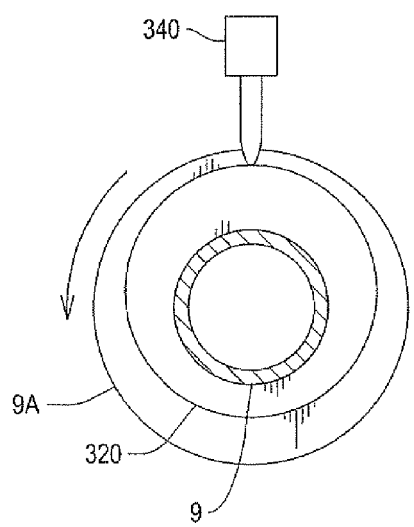 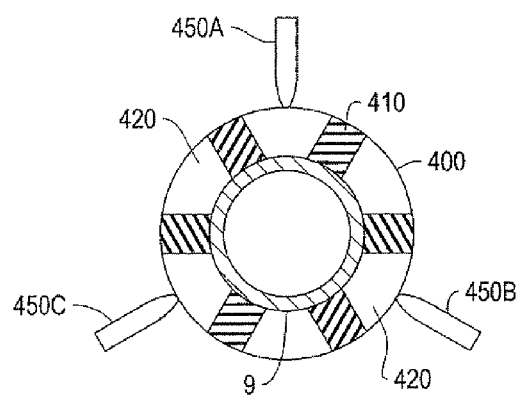
FIG. 15        FIG. 16

SURGICAL CUTTING INSTRUMENT WITH ELECTROMECHANICAL CUTTING

BACKGROUND

This disclosure relates to surgical instruments, and in particular to surgical cutting instruments having mechanical cutting blades and one or more electrodes for providing surgical energy to the treatment area (e.g., for coagulation, vaporization of tissue, and/or other treatment effects).

Surgical apparatus used to shave, cut, resect, abrade and/or remove tissue, bone and/or other bodily materials are known. Such surgical apparatus can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube. The cutting window of the outer tube exposes the cutting surface of the inner tube (typically located at a side of the distal end of the inner tube) to tissue, bone and/or any other bodily materials to be removed. A powered handpiece is used to rotate the inner tube with respect to the outer tube while an outer tube hub (connected to the proximal end of the outer tube) is fixed to the handpiece and an inner tube hub (connected to the proximal end of the inner tube) is loosely held by the powered handpiece and is rotated by a motor of the handpiece.

In some instruments, the inner tube is hollow and has a cutting window on a side surface near its distal end such that tissue, bone, etc., will be cut or shaved as the cutting window of the inner tube aligns with and then becomes misaligned with the cutting window of the outer tube as the inner tube is rotated within the outer tube. In this regard, it can be said that the cutting device nibbles or takes away small pieces of the bone, tissue, etc., as the inner tube is rotated within the outer tube.

In some instruments, a vacuum is applied through the inner tube such that the bodily material that is to be cut, shaved, etc., is drawn into the windows of the inner and outer tubes when those windows become aligned, thereby facilitating the cutting, shaving, etc., of the tissue, which then travels through the inner tube due to the suction. It also is common to supply an irrigation fluid, which can include a liquid, to the surgical site via a passage provided between the inner and outer tubes.

Microdebrider shaver blades are common instruments used in endoscopic surgery. The shaver blade delivers high speed mechanical cutting of tissue at a specified area of anatomy that the surgeon can reach through a minimally invasive incision or natural orifice. One challenge during procedures using such instruments can be the slowing down or stopping of bleeding (hemostasis) during the procedure. One solution for maintaining proper hemostasis during a procedure is to utilize an electrocautery instrument that can be used inside the same minimally invasive surgical corridor. In a minimally invasive procedure, every time the surgeon exchanges the cutting instrument for the electrocautery instrument there is a corresponding increase in the time required to perform the procedure and there is a risk of traumatizing the anatomy due to the exchange of the instruments. Thus, it is convenient to combine the mechanical cutting and electrocautery instruments to form one instrument performing both functions. By providing a microdebrider shaver blade that also can perform electrocautery, the need to perform tool exchanges at the surgical site is reduced and can even be eliminated.

There are two standard types of electrocautery: bipolar and monopolar. Monopolar cautery uses one electrode at the surgical site and then relies on a neutral electrode placed somewhere else on the patient (typically on the skin of the patient) to help disburse the energy enough to pass the energy safely through the patient. Bipolar cautery does not use a separate neutral electrode. Instead, bipolar cautery delivers the energy and returns the energy through the device using two electrodes at the surgical site. That is, a bipolar device will provide two electrodes at the surgical site, one active electrode and one return electrode.

It is known to provide microdebrider shaver blades with bipolar energy electrodes to perform the electrocautery. As is known, cutting or shaving takes place by rotating (or oscillating with some devices) the inner cutting blade while suction is applied through the device. An electrical signal appropriate for achieving electrocautery is applied to the active electrode so that tissue is cauterized to achieve hemostasis during use of the device.

It also is known to perform surgical cutting using only electrical energy. For example, a cutting device such as an electrical scalpel can be used to completely remove the surgical area. Such devices are used, for example, to perform tonsillectomies. These electro-surgical devices generally have no moving parts to engage the tissue. Thus, these procedures in which electrical energy is used to remove tissue are often performed "open" and make use of manual grasping instruments to bring the tissue into contact with the cutting electrode.

SUMMARY

In accordance with some aspects of the invention, a mechanical cutting device which makes use of mechanical motion and suction to engage tissue also applies a cutting energy sufficient to vaporize the tissue. When the device uses a rotary motion (for example, the device includes a rotating inner blade having a sideward-facing cutting window that rotates within an outer cutting blade having a sideward-facing cutting window) the rotary motion (of the inner blade) can be much slower than typical microdebrider speeds (in one illustrative example, speeds as low as about 60 rpm or less). The rotation and suction are used to engage the tissue (sucking tissue into the cutting windows when the cutting windows of the inner and outer blades are aligned), and then the cutting member (or members) function as an electrode and have an electrical cutting signal applied thereto so that the cutting member (or members) electrically cut the tissue as one of the cutting members (i.e., the inner cutting blade) rotates. The electromechanical action may provide a cleaner, more precise cut of larger "bites" of tissue compared with mechanical cutting. Purely mechanical cutting at higher speeds often chews (multiple rotations required to take a large "bite") tissue, and may be limited to smaller "bites" of tissue due to the relatively small time frame in which the cutting window is open.

Preferably, the electrical cutting signal is only applied as the windows become aligned and then become misaligned by rotation (or other oscillating motion) of the inner cutting blade until the cutting of the tissue is completed. The cutting signal preferably is then stopped after the cutting windows become misaligned so that undesired tissue vaporization does not occur. While the cutting windows are misaligned, a coagulation signal nonetheless can be supplied to the cutting member so that the device functions as an electrocautery device thereby minimizing or eliminating bleeding.

The electrocautery-inducing signal preferably is applied during only part of the rotation of the inner cutting blade. Preferably, the electrocautery-inducing signal is applied only when the cutting windows are misaligned (that is, the electrocautery-inducing signal is not applied when tissue can be sucked into the aligned windows). Applying the electrocautery-inducing signal at all times can increase the temperature of the tip of the instrument, causing eschar buildup (burned tissue/blood buildup) and potentially galling the mechanical bearing surfaces of the cutting instrument. Intermittently applying the electrocautery-inducing signal reduces the amount of energy delivered to the tissue, reducing heat buildup of the instrument, thereby minimizing or eliminating eschar buildup. This aspect of the invention is applicable to mechanical cutting microdebriders with or without the electro-cutting (tissue vaporization) capability.

In accordance with some aspects of the invention, a surgical cutting instrument includes a first cutting blade, a second cutting blade, at least one first electrode and control circuitry. The first cutting blade has a tubular body with a distal end and a proximal end, and includes a cutting window that is sideward-facing disposed at the distal end of the first cutting blade. The cutting window includes a cutting edge. The second cutting blade is movably disposed inside the first cutting blade and has a distal cutting portion that, together with the cutting edge of the cutting window, cuts tissue by moving within the first cutting blade. The at least one first electrode is located adjacent to at least the cutting edge at the distal end of the first cutting blade. The control circuitry is configured to control an electrical power signal supplied to the at least one first electrode. The control circuitry varies the electrical power signal based on a position of the second cutting blade relative to the first cutting blade, a rotating speed of the second cutting blade, or both.

A surgical cutting instrument having the above structure can selectively vaporize tissue or coagulate tissue depending on the electrical power signal supplied to the at least one first electrode by the control circuitry.

According to some embodiments, the second cutting blade moves between a first position, at which the tissue to be cut is permitted to enter the cutting window of the first (outer) cutting blade, and a second position at which the tissue has been cut by the cutting window. The control circuitry supplies a first electrical power signal at least part of the time while the second cutting blade is in the first position, and supplies a second electrical power signal, which is different from the first electrical power signal, at least part of the time while the second cutting blade is in the second position. The first electrical power signal, for example, causes the tissue to be cut/vaporized. In accordance with some embodiments, the second electrical power signal causes the tissue to be coagulated/cauterized.

According to other embodiments, the second electrical power signal is a zero power signal (that is, the second electrical power signal does not cause tissue vaporization or coagulation).

According to some embodiments, the electrical power signal supplied by the control circuitry is a monopolar signal.

According to some embodiments, an insulation layer is disposed over at least a portion of the distal end of the first cutting blade. In addition, at least one second electrode is located over at least a portion of the insulation layer and is electrically coupled to the control circuitry. In such an arrangement, the electrical power signal supplied by the control circuitry is a bipolar signal.

According to preferred embodiments, suction is applied through the cutting window at the distal end of the first cutting blade.

According to some embodiments, the second cutting blade rotates about a longitudinal axis of the surgical cutting instrument.

According to other embodiments, the second cutting blade reciprocates in a longitudinal direction of the surgical cutting instrument.

According to some embodiments, the control circuitry includes a sensor that senses a position of the second cutting blade relative to the first cutting blade, a rotational speed of the second cutting blade, or both. The control circuitry also preferably includes a processor that varies the electrical power signal based on the sensed position of the second cutting blade relative to the first cutting blade.

According to some embodiments, the control circuitry includes at least one moving electrical contact coupled to the second cutting blade and at least one fixed contact that intermittently contacts the at least one moving electrical contact as the second cutting blade moves.

According to some embodiments, the second cutting blade moves between a first position at which at least a part of the distal cutting portion faces the cutting window and a second position at which the distal cutting portion does not face the cutting window. In addition, the control circuitry supplies a first electrical power signal at least part of the time while the second cutting blade is in the first position, and a second electrical power signal, which is different from the first electrical power signal, at least part of the time while the second cutting blade is in the second position. The first electrical power signal can be sufficient to cause vaporization (electrical cutting) of tissue. The second electrical power signal can be sufficient to cause coagulation.

A surgical cutting instrument according to another aspect of the invention includes a first cutting blade, a second cutting blade, at least one first electrode, a sensor and a processor. The first cutting blade has a tubular body with a proximal end and a distal end, and a cutting window is disposed at a side of the first cutting blade near the distal end. The second cutting blade has a tubular body with a proximal end and a distal end, and a cutting window is disposed at a side of the second cutting blade near the distal end. The second cutting blade is rotatably disposed inside of the first cutting blade such that the surgical cutting instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade. The at least one first electrode is located adjacent to at least the cutting window at the distal end of the first cutting blade. The sensor senses a rotational position of the second cutting blade relative to the first cutting blade. The processor controls an electrical power signal supplied to the at least one first electrode at least partially based on the sensed rotational position of the second cutting blade relative to the first cutting blade. In particular, the processor supplies (i) a first electrical power signal at least part of the time while the cutting windows of the first and second cutting blades are aligned with each other, and (ii) a second electrical power signal, which is different from the first electrical power signal, at least part of the time while the cutting windows of the first and second cutting blades are not aligned with each other. The first electrical power signal can be sufficient to cause vaporization (electrical cutting) of tissue. The second electrical power signal can be sufficient to cause coagulation.

A surgical cutting instrument according to another aspect of the invention includes first and second cutting blades, at least one first electrode, and control circuitry. The first cutting blade has a tubular body with a proximal end and a distal end, and a cutting window is disposed at a side of the first cutting blade near the distal end. The second cutting blade has a tubular body with a proximal end and a distal end, and a cutting window is disposed at a side of the second cutting blade near the distal end. The second cutting blade is rotatably disposed inside of the first cutting blade such that the surgical cutting instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade. The at least one first electrode is located adjacent to at least the cutting window at the distal end of the first cutting blade. The control circuitry is coupled to at least the second cutting blade and supplies an electrical power signal to the at least one first electrode. In particular, the control circuitry supplies (i) a first electrical power signal at least part of the time while the cutting windows of the first and second cutting blades are aligned with each other, and (ii) a second electrical power signal, which is different from the first electrical power signal, at least part of the time while the cutting windows of the first and second cutting blades are not aligned with each other. The first electrical power signal can be sufficient to cause vaporization (electrical cutting) of tissue. The second electrical power signal can be sufficient to cause coagulation.

BRIEF DESCRIPTION OF THE DRAWINGS

Various exemplary embodiments of the disclosed surgical instrument will be described in detail with reference to the following drawings in which:

FIG. 14 shows an embodiment that includes LVDTs to determine the relative positions of the inner and outer cutting blades;

FIG. 15 is an end view of the FIG. 14 inner cutting blade;

FIG. 16 shows another type of sensor arrangement for sensing the position of a cutting blade;

DETAILED DESCRIPTION OF THE EMBODIMENTS

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. All exemplary embodiments of the invention are intended to be used in any applicable field of endeavor.

Figure 1:
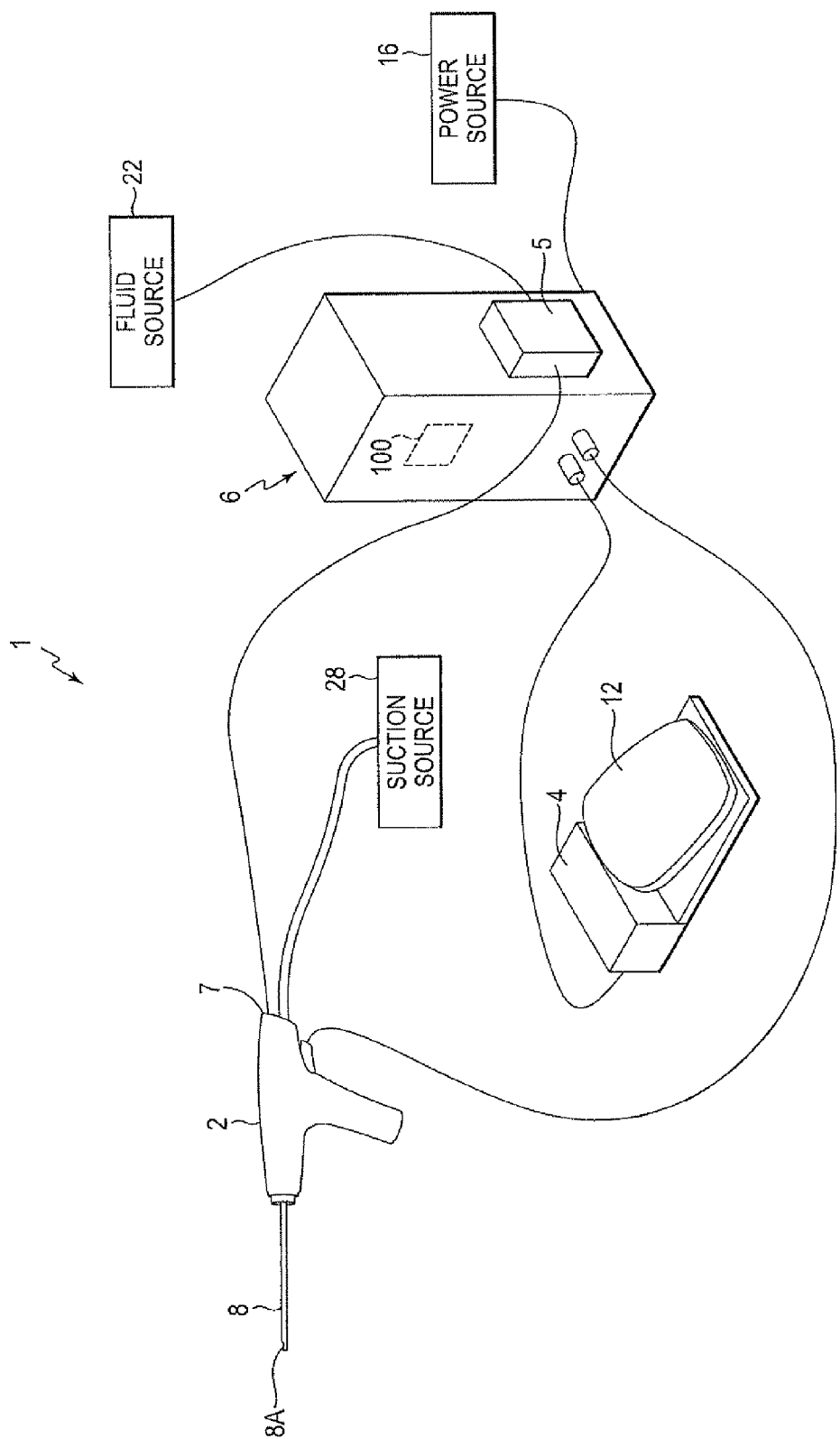
FIG. 1 illustrates a perspective view of a powered surgical instrument system that incorporates a surgical instrument, control unit, fluid source and suction source.

FIG. 1 is a schematic of a powered surgical instrument system. Except for the rotation sensor system, the electrodes and the control system, to be described hereafter, the system may be in accordance with the system described in U.S. Pat. No. 7,247,161, the disclosure of which is incorporated herein by reference in its entirety. Another system to which the invention is applicable is described in U.S. Pat. No. 7,318,831, the disclosure of which is incorporated herein by reference in its entirety. As shown in FIG. 1, the powered surgical instrument system 1 includes a handle (or handpiece) 2, a footswitch 4 (with pedal 12), fluid (liquid and/or gas) source 22, suction source 28, a control unit 6, fluid pump 5 and a fluid inlet/irrigation outlet 7. The system is supplied with power from a power source 16 such as a wall outlet. The suction source 28 may be an external suction source such as provided by attachment to a facility suction outlet provided on a wall. The handpiece 2 is connected, at its distal end, to a surgical instrument 8. The surgical instrument 8 in this embodiment includes a cutting tip at its distal end 8A that is used, for example, to cut, shave, remove, resect and/or abrade tissue, bone and/or other bodily materials. One or more electrodes (to be discussed later) are provided on the surgical instrument 8. In order to simplify the drawings, the electrodes are not labeled in FIGS. 1-5.

Figure 2:
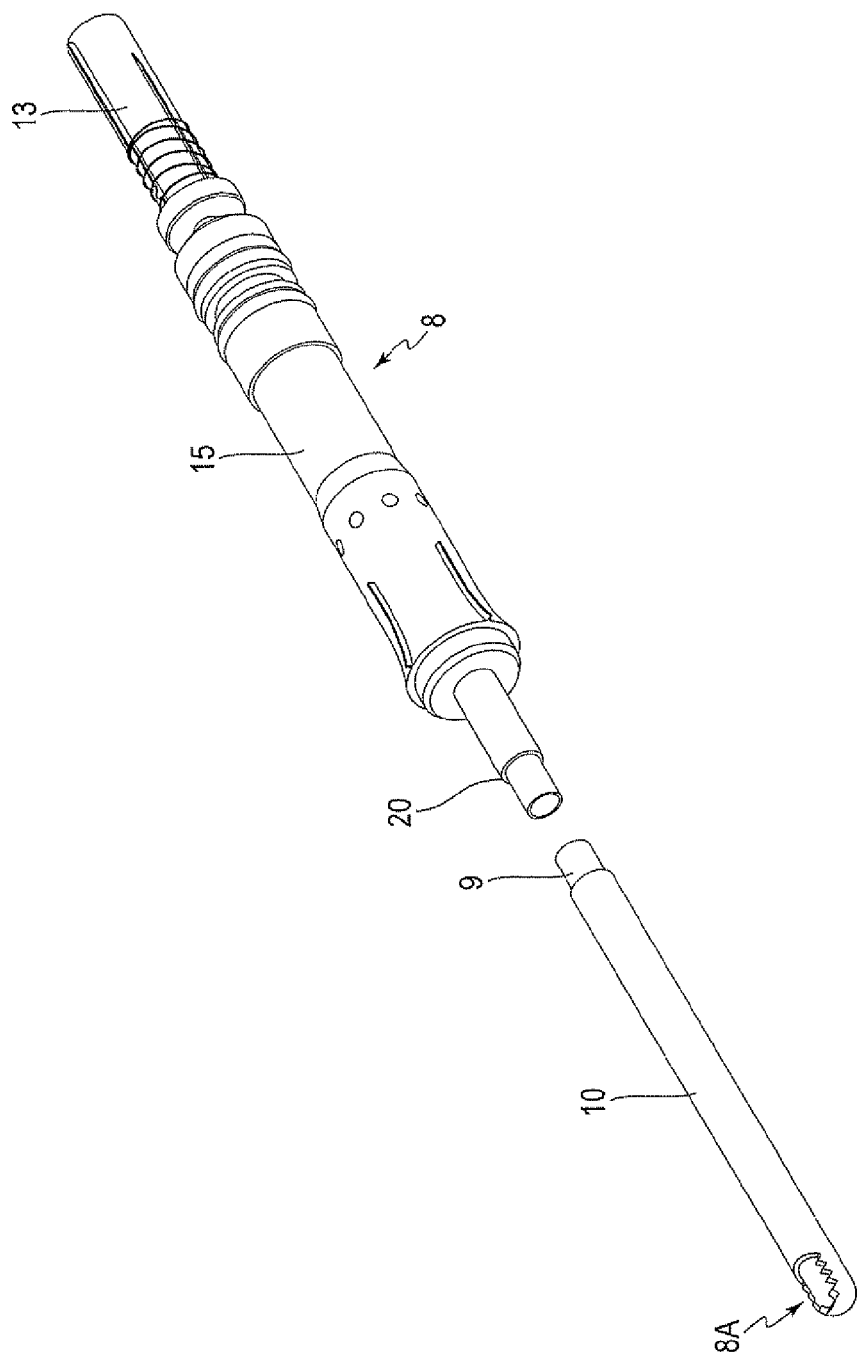
FIG. 2 is a perspective view of an exemplary embodiment of a surgical instrument in accordance with the present disclosure.

FIG. 2 illustrates a perspective view of an exemplary embodiment of the surgical instrument 8 in accordance with aspects of the invention. The instrument 8 incorporates an inner tube 9 and an outer tube 10. In this exemplary embodiment, an inner tube hub 13 is formed on the second end 14 (see FIG. 3) of the inner tube 9 and an outer tube hub 15 is formed on the second end 17 (see FIG. 3) of the outer tube 10. For purposes of this disclosure, each tube 9/10 and its hub 13/15 are collectively referred to as a "tube" or "member." The inner tube 9 is inserted into a fluid passage 20 formed within the outer tube 10 so that the inner tube 9 is co-axially disposed within the outer tube 10 until the external distal tip of the inner tube 9 contacts the internal distal surface of the outer tube 10. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube. Irrigation liquid can be supplied to the surgical site by supplying the liquid to the passage 20 via an inlet 26.

The inner and outer tube hubs 13, 15 couple the inner and outer tubes 9, 10, respectively, to the handpiece 2. Once coupled to the handpiece 2, the outer tube 10 will be fixed relative to the handpiece 2, but the inner tube 9 will be rotatable relative to the outer tube 10 and the handpiece 2.

Figure 3:
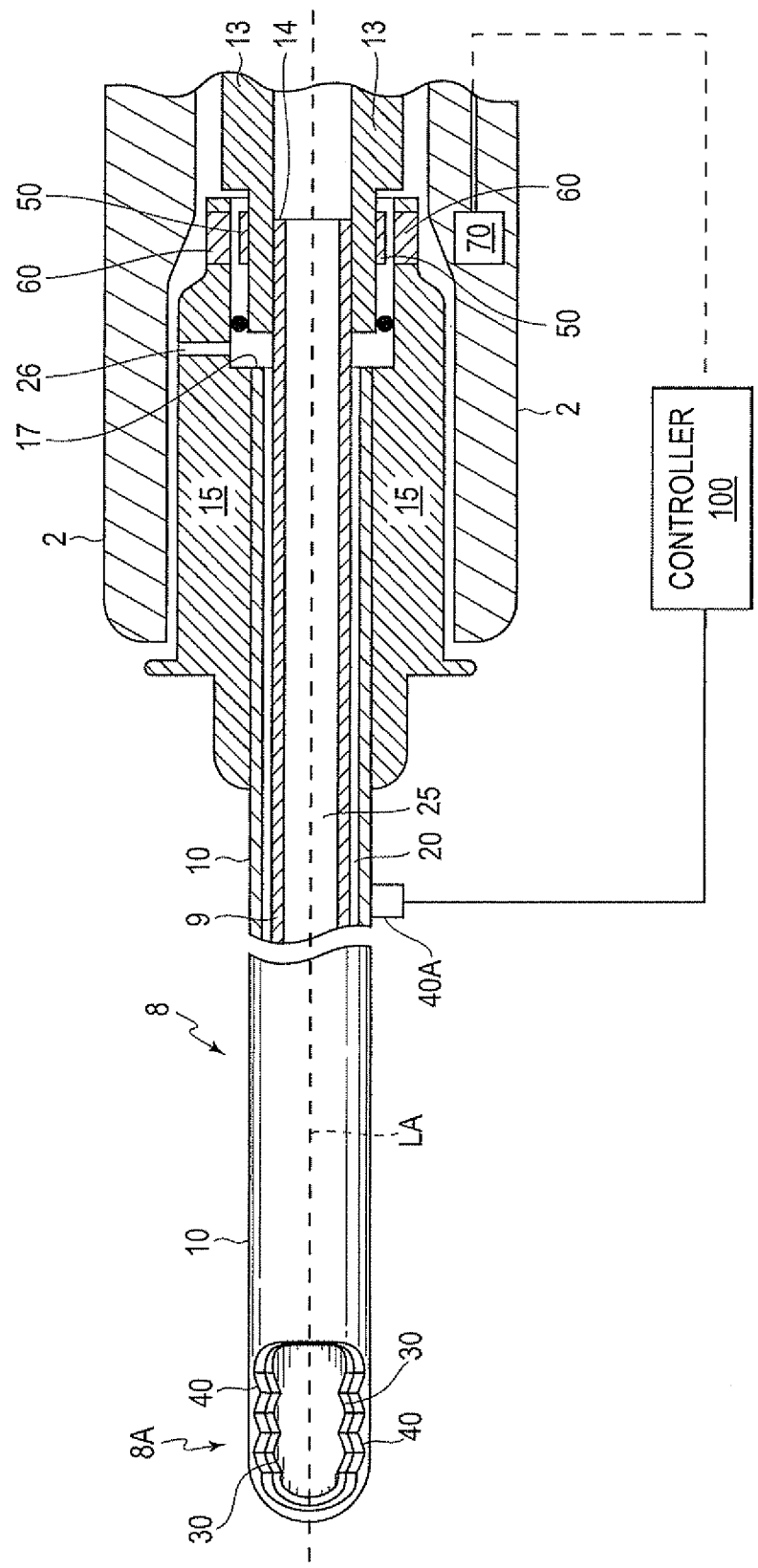
FIG. 3 is a side view, partially in perspective and partially in cross-section, of a surgical instrument having a rotation sensor system in accordance with an embodiment of the present disclosure.
Figure 4:
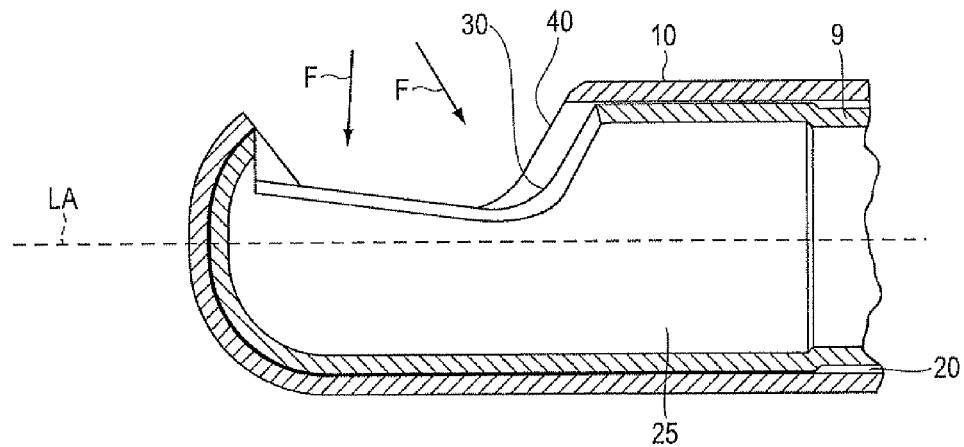
FIG. 4 is a side, cross-sectional view of the FIG. 3 surgical instrument distal tip with the cutting windows being in complete alignment.
Figure 5:
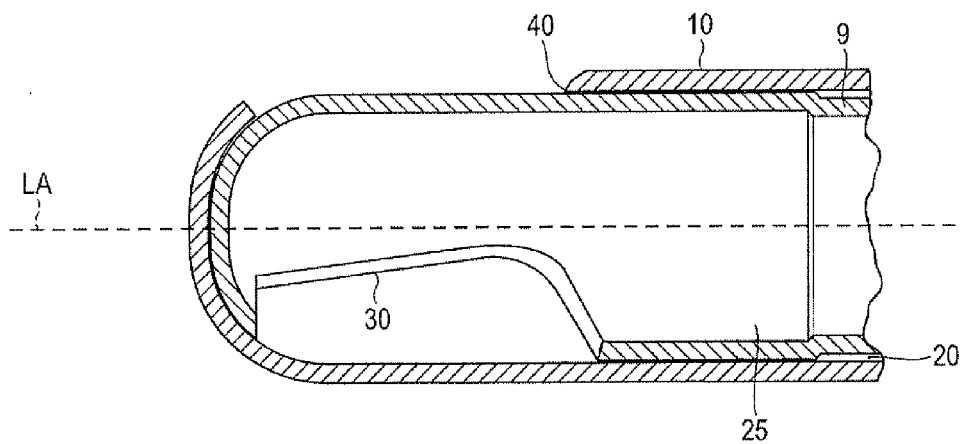
FIG. 5 is a side, cross-sectional view similar to FIG. 4, but with the cutting windows being in complete mis-alignment so that suction is not applied through the cutting windows.

Referring to FIG. 3, which shows a perspective view of the tip 8a and a cross-sectional view of the handpiece 2 and proximal ends of the cutting blades 9 and 10, the outer tube 10 includes a cutting window 40 disposed at a side of its distal end. Thus, the outer tube 10 can be referred to as a first cutting blade. The inner tube 9 also includes a cutting window 30 disposed at a side of its distal end. Thus, the inner tube 9 can be referred to as a second cutting blade. The edges of the cutting windows 30 and 40 can be serrated, smooth or a combination of serrated and smooth to form cutting surfaces. As mentioned previously, the inner cutting blade 9 rotates within the outer cutting blade 10, and thus as the inner cutting blade 9 rotates, the cutting windows 30 and 40 become aligned with each other as shown in FIG. 4 and then become misaligned with each other as shown in FIG. 5. When the cutting windows 30 and 40 are misaligned with each other as shown in FIG. 5, the side of the inner tube 9 distal tip opposite from the cutting window 30 blocks the cutting window 40 of the outer cutting blade 10.

The first, or outer cutting blade 10 thus is an outer tube having a proximal end and a distal end, with a cutting window 40 disposed at a side of the first cutting blade 10 near the distal end.

The inner, second cutting blade 9 is a tubular body having a proximal end and a distal end, with cutting window 30 disposed at a side of its distal end. As mentioned previously, the second, inner cutting blade 9 is rotatably disposed inside of the first, outer cutting blade 10 such that the surgical instrument 8 cuts tissue by rotating the second, inner cutting blade 9 within the first, outer cutting blade 10 while a vacuum is applied through an internal bore 25 of the cutting blade 9 to draw the tissue into the cutting windows 30 and 40 of the cutting blades 9 and 10 and sever the tissue by rotation of the cutting blade 9. Thus, the cutting blade 9 is an inner rotating member having a cutting member near its distal end. The inner rotating member need not be a tube. For example, the inner rotating member could be a shaft with a cutting member at its distal end. With such an arrangement, suction would be applied through the hollow outer tube 10. Furthermore, the inner cutting member could be a tube or shaft that reciprocates in the direction of longitudinal axis LA instead of rotating. The inner member tube or shaft could rotate and reciprocate longitudinally.

FIG. 3 also shows a rotation sensor system in accordance with an embodiment of the invention. The rotation sensor system of this embodiment is described in more detail in U.S. patent application Ser. No. 13/251,493 filed Oct. 3, 2011, the disclosure of which is incorporated herein by reference in its entirety. In order to detect the rotational position of inner cutting blade 9 relative to outer cutting blade 10, a rotation sensor system is provided. The rotation sensor system includes a magnetic member 50 provided on the inner cutting blade 9 near the proximal end of the inner cutting blade 9 (on hub 13), a magnetically permeable member 60 provided on the outer cutting blade 10 near the proximal end of the outer cutting blade (on hub 15), and a sensor 70 provided on the handpiece 2. The sensor 70 senses the magnetic flux of the magnetically permeable member 60 adjacent to the sensor 70. The output of the sensor 70 is provided to a controller 100, which is part of the control unit 6, and includes, for example, a microprocessor (CPU), working memory (RAM) and storage (ROM) in which appropriate programs for using the output of sensor 70 are stored.

Figure 6A:
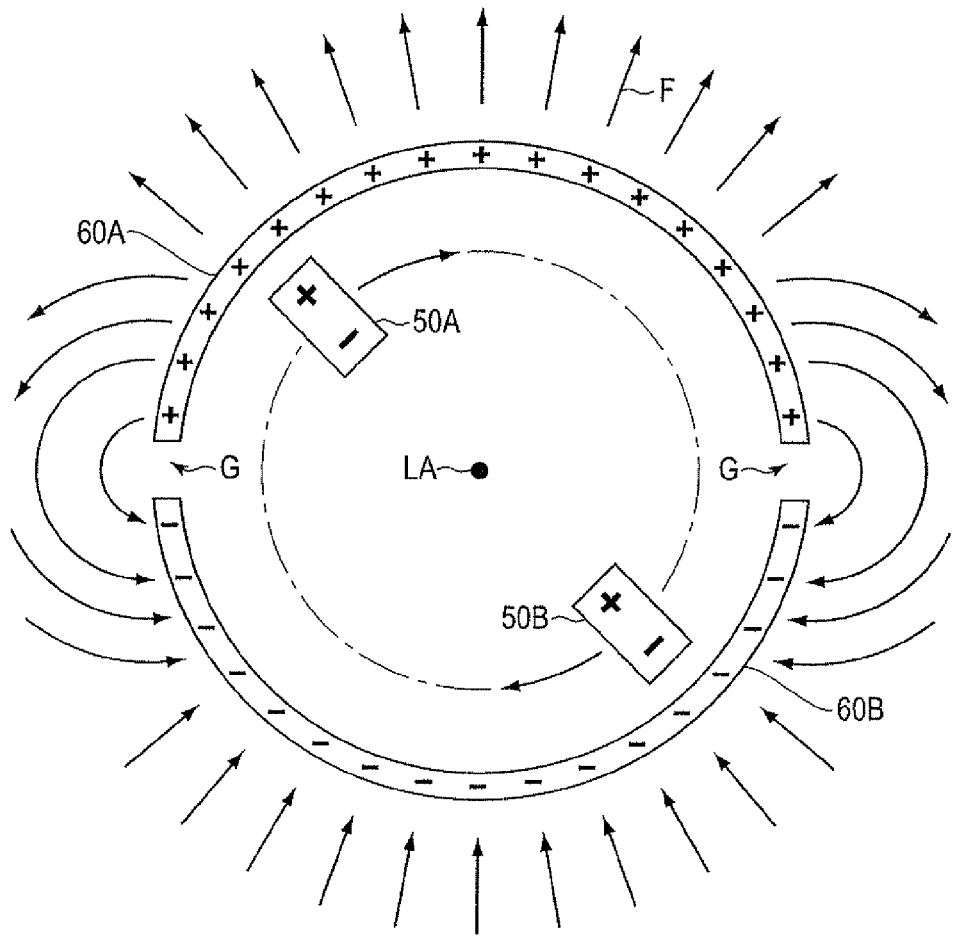
FIG. 6A is a cross-sectional view showing the magnetic members of an inner cutting blade and the magnetically permeable pieces of ferromagnetic material of the outer cutting blade.
Figure 6B:
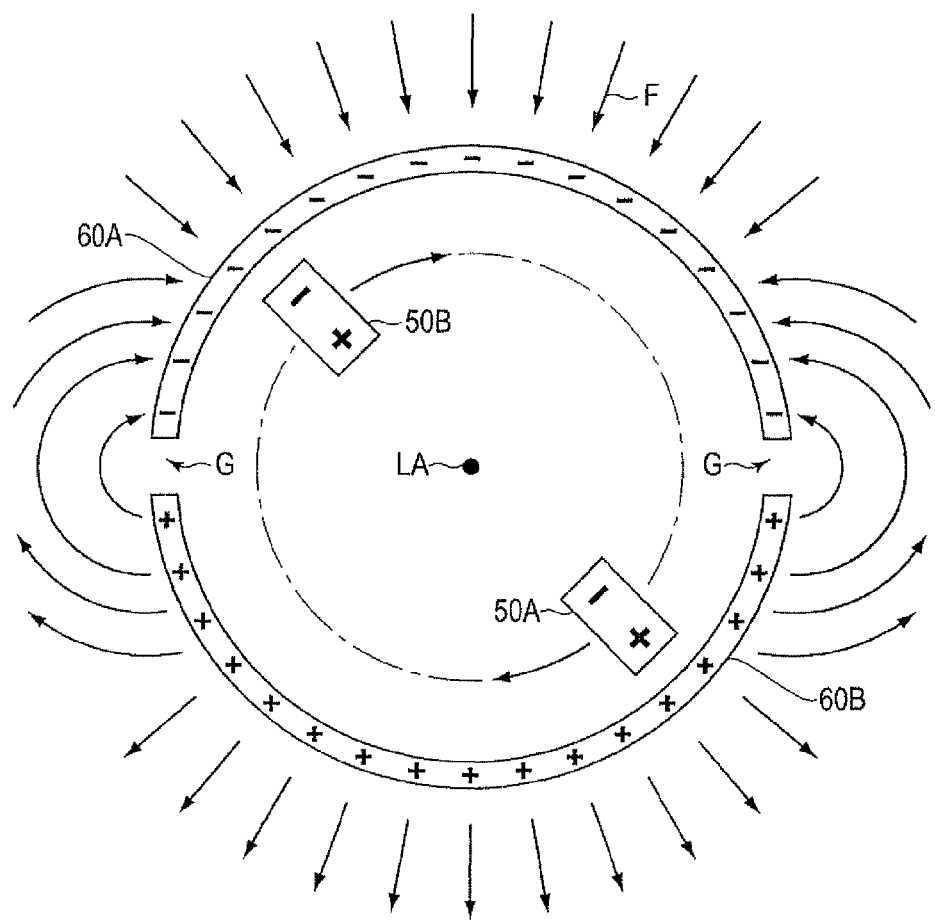
FIG. 6B is a view similar to FIG. 6A except that the inner cutting blade has rotated by 180° such that the direction of the magnetic flux induced in the magnetically permeable pieces has reversed.

The manner in which one embodiment functions will be described in conjunction with FIGS. 3, 6A and 6B. The handpiece 2 includes a longitudinal axis LA. As shown in FIG. 3, the magnetic member 50, the magnetically permeable member 60 and the sensor 70 are radially aligned with each other with respect to the longitudinal axis of the handpiece 2. In particular, the magnetic member 50 is disposed radially inward of the magnetically permeable member 60. (That is, magnetic member 50 is closer to the longitudinal axis LA than is the magnetically permeable member 60.) In addition, the magnetically permeable member 60 is disposed radially inward of the sensor 70. As shown in FIGS. 6A and 6B, the magnetic member 50 includes two oppositely polarized magnets 50a and 50b disposed at diametrically opposite positions relative to the longitudinal axis LA of the inner cutting blade 9, which also corresponds to the longitudinal axis LA of the handpiece 2. The magnets 50a and 50b are positioned such that a polarity of an outwardly-facing pole of a first one of the magnets (50a) is opposite to a polarity of an outwardly-facing pole of a second one of the magnets (50b). If the symbol + signifies the North pole and the symbol − signifies the South pole, as shown in FIGS. 6A and 6B, magnet 50a is arranged with its North pole facing radially outward, whereas magnet 50b is arranged with its South pole facing radially outward.

The magnetically permeable member 70 includes two semicircular pieces 60a and 60b of magnetically permeable material such as a ferromagnetic material (for example, NiFe). The two semicircular pieces 60a and 60b are located on opposite circumferential segments near the proximal end of the hub 15 associated with the outer cutting blade 10. Each of the pieces 60a and 60b extends almost one-half around the circumference of the hub 15. Opposing ends of the two semicircular pieces of ferromagnetic material 60a, 60b are separated from each other by gaps G as shown in FIGS. 6A and 6B. Magnetic flux will be induced in the ferromagnetic pieces 60a and 60b based on the polarity of the magnet surface (of magnets 50a and 50b) that is located adjacent to each particular ferromagnetic piece. When the inner cutting blade 9 is positioned with its magnets 50a and 50b as shown in FIG. 6A, magnetically permeable material piece 60a will have the same magnetic polarity as the outer face of magnet 50a, whereas magnetically permeable piece 60b will have the same magnetic polarity as the outer face of magnet 50b. When the inner cutting blade 9 has rotated by 180°, as shown in FIG. 6B, the polarities of the magnetically permeable material pieces 60a and 60b will be the opposite of that shown in FIG. 6A. Thus, as the inner cutting blade 9 rotates relative to the outer cutting blade 10, the polarities of the magnetically permeable material pieces 60a and 60b will fluctuate (instantaneously switch) between the states shown in FIGS. 6A and 6B, with their polarities switching each time the magnets 50a and 50b pass by the gaps G. Accordingly, the sensor 70 disposed adjacent to a portion of the magnetically permeable material 60 will sense the magnetic flux of the magnetically permeable material adjacent thereto, and thus will output a signal that fluctuates as the inner cutting blade 9 rotates.

Figure 7:
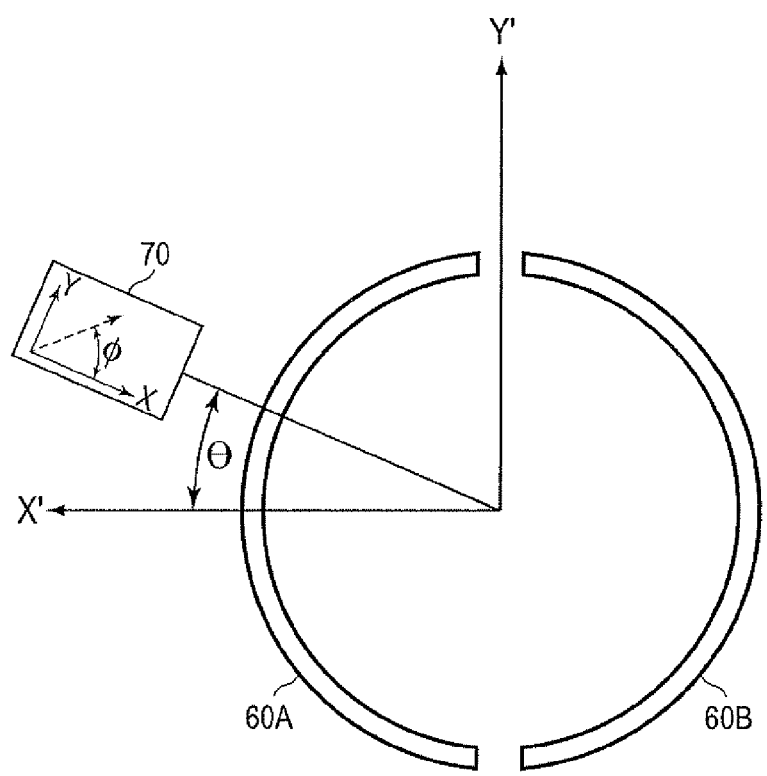
FIG. 7 shows a dual axis linear magnetic sensor positioned relative to the magnetically permeable member of the outer cutting blade.

FIG. 7 shows one example of sensor 70. According to a preferred embodiment, sensor 70 is a dual axis linear magnetic sensor that senses magnetic flux in two perpendicular directions (the X direction and the Y direction). The sensor 70 is positioned relative to the magnetically permeable material pieces 60a and 60b such that one of its measurement axes (the X axis shown in FIG. 7) is normal to the adjacent surface of the magnetically permeable structure.

It has been determined that, as long as the sensor 70 is positioned radially close enough to the magnetically permeable pieces 60a and/or 60b, the sensor 70 can effectively sense the instantaneous switching of the polarities of the magnetically permeable material located adjacent to the sensor regardless of where the sensor is located around the circumference of the magnetically permeable member defined by the magnetically permeable material pieces 60a and 60b. Accordingly, the disclosed arrangement is very effective at detecting the position of the inner cutting blade 9 relative to the outer cutting blade 10 even if the rotational orientation of the outer cutting blade 10 relative to the handpiece 2 (and thus relative to the sensor 70) is changed.

Because the positional relationship between the magnets 50a and 50b and the cutting window 30 of the inner cutting blade 9 is fixed, and because the positional relationship between the magnetically permeable material pieces 60a and 60b and the cutting window 40 of the outer cutting blade 10 is fixed, the signal output by sensor 70 can be interpreted by signal processing software and/or hardware of the controller 100 to determine the position of the cutting windows 30 and 40 relative to each other. For example, referring to FIG. 3, if the cutting window 40 of outer cutting blade 10 faces out of the page, the magnetically permeable material pieces 60a and 60b could be arranged on the hub 15 so that the gaps G are on the top side and the bottom side in FIG. 3 of the hub 15. Similarly, if the cutting window 30 of the inner cutting blade 9 faces out of the page as shown in FIG. 3, the magnets 50a and 50b could be arranged so that they extend from the upper side and the lower side of the hub 13 in FIG. 3. Accordingly, each time the magnets 50a and 50b are aligned with the gaps G, the windows 30 and 40 either will be completely aligned as shown in FIG. 3 and FIG. 4, or completely misaligned as shown in FIG. 5. Thus, the position of the inner blade relative to the outer blade can be determined. The signal output by sensor 70 also can be used to determine the rotational speed of the inner cutting blade.

Figure 8A:
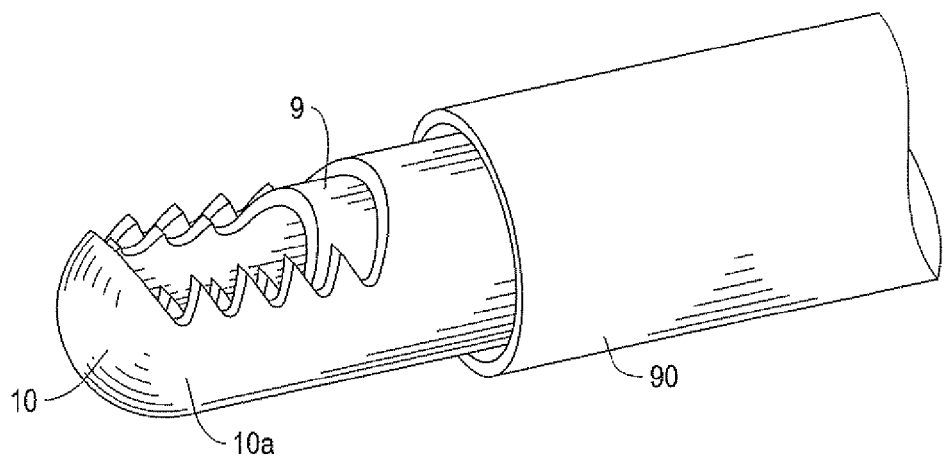
FIGS. 8A-8C show one embodiment in which the cutting instrument is provided with an electrode for receiving a monopolar signal.
Figure 8B:
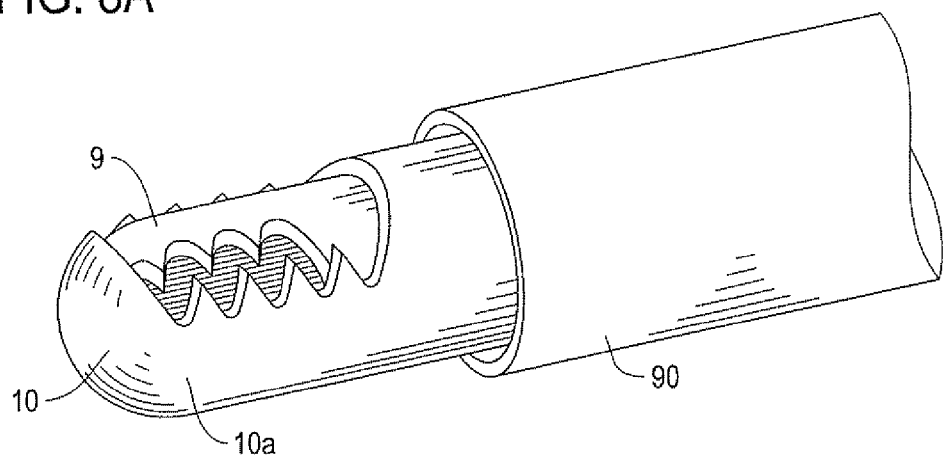
Figure 8C:
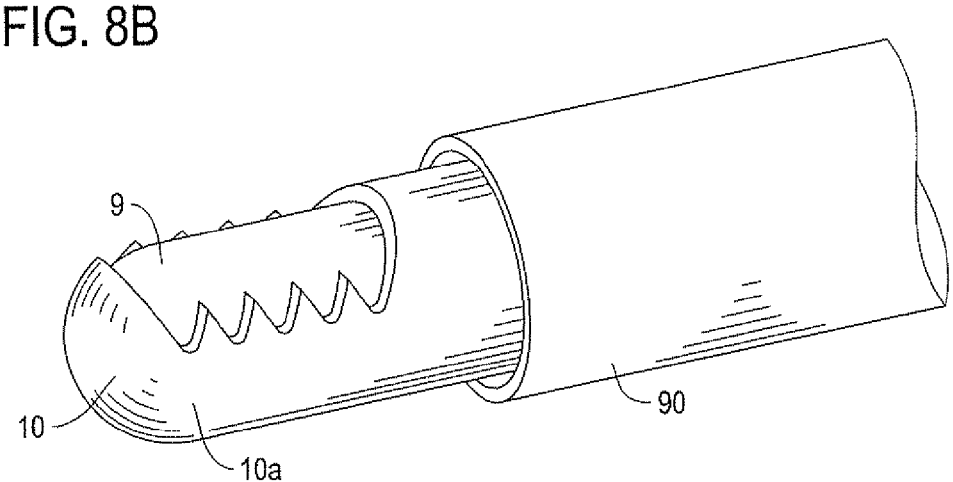

FIGS. 8A-8B show an embodiment in which the control circuitry (included in controller 100) applies a monopolar signal to at least one electrode provided adjacent to the cutting edge of the cutting window 40 at the distal end of the first (outer) cutting blade 10. Because the outer cutting blade 10 can be made of an electrically conductive material such as stainless steel, an electrical signal sufficient to perform electrical cutting (vaporization of tissue) or coagulation can be provided to the area adjacent to the cutting window 40 of the outer cutting blade 10 simply by providing an electrical connector 40A (see FIG. 3) near the proximal end of the outer cutting blade 10. The electrical connector 40A is attached to the controller 100 and is provided with the appropriate signal (vaporization or coagulation) based on the detected position of the inner cutting blade 9 relative to the outer cutting blade 10 in accordance with one embodiment of the invention. As shown in FIGS. 8A-8C, an insulative sheath 90 is provided over the outer cutting blade 10 so that the electrical energy (for vaporization or coagulation) is provided to tissue only at the distal end of the outer cutting blade 10. In this regard, the distal end of cutting blade 10 functions as an electrode 10A.

When the cutting windows 30 and 40 of the inner and outer cutting blades are in complete alignment as shown in FIG. 8A, the controller 100 sends a first electrical signal that is sufficient to cause vaporization of tissue to the electrode 10A formed at the distal end of the outer cutting blade 10. The first electrical signal continues to be applied as the inner cutting blade 9 rotates from the open position shown in FIG. 8A to the closed position shown in FIG. 8C. That is, the first electrical signal, which is sufficient to induce tissue vaporization, also is applied while the instrument is in the state shown in FIG. 8B with the cutting window 40 partially closed due to rotation of the inner cutting blade 9. Thus, tissue is cut due to the mechanical cutting action of the cutting windows 30 and 40 and due to the electrical vaporization signal provided to the electrode 10A. Once the window 40 of the outer cutting blade 10 becomes completely closed due to rotation of the inner cutting blade 9, supply of the first electrical signal is stopped. Supply of the first electrical (vaporization) signal can start just before the windows 30/40 become aligned (or when or slightly after they become aligned) and can be stopped when (or slightly before or after) the cutting window 40 becomes completely blocked by the inner cutting blade 9.

If coagulation is desired, then a second electrical signal, different from the first electrical signal, is provided by the controller 100 to the electrode 10A while the instrument is not performing any mechanical (or electrical) cutting of tissue. The second electrical signal is sufficient to achieve tissue coagulation, but preferably is not sufficient to achieve vaporization of tissue. Depending on the surgical procedure, hemostasis may not be an issue, and thus the value of the second electrical signal could be zero such that no coagulation energy is applied. If coagulation is desired, then the value of the second electrical signal can be a well known value effective at achieving coagulation of tissue.

In the embodiment shown in FIGS. 8A-8B, the material of the outer cutting blade 10 functions as an electrode. In order to restrict the area of the patient that receives the electrical energy, an electrically non-conductive coating or shrink tubing can be formed over the outer surface of blade 10, leaving the portion of the blade that is to function as the electrode uncovered. Alternatively, a separate electrically-conductive layer can be provided over the material that forms the outer cutting blade 10 to form the electrode 10A. The electrically-conductive material could be provided over the entire outer surface of the outer cutting blade 10, or it could be provided only at the distal end of the outer cutting blade 10 adjacent to the cutting window 40.

The embodiment shown in FIGS. 8A-8C is a monopolar embodiment and thus a separate return electrode is provided, for example, as a patch attached to the skin of the patient. The invention also is applicable to bipolar systems.

Figure 9:
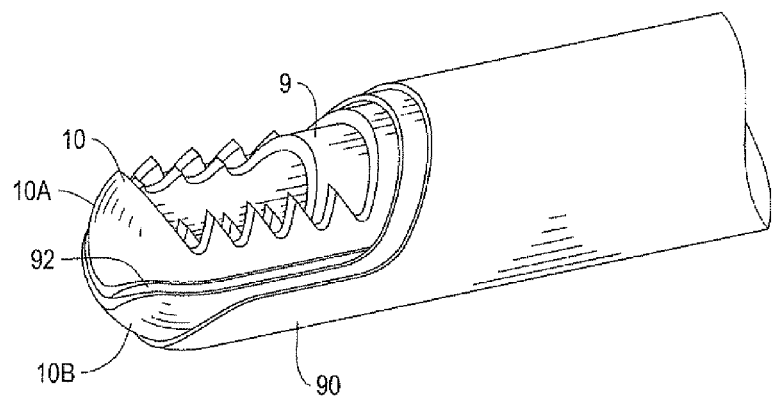
FIG. 9 shows an embodiment in which the cutting instrument is provided with two electrodes for receiving a bipolar signal.

FIG. 9 shows an example of a bipolar system. In FIG. 9, the distal end of the outer cutting blade 10 forms an electrode 10A, which will function as a return electrode of the bipolar system. An insulation layer 92 is formed over the outer cutting blade 10. Another electrode 10B is formed as a layer of electrically-conductive material over the insulation layer 92. Electrode 10B can function as the active electrode and will receive the signal (for example, to perform vaporization or coagulation) from the controller 100. An outer insulation layer 90 is formed over the electrode layer 10B and protects areas of the patient which are not to be subjected to coagulation or cutting from receiving energy from the electrode 10B.

In the embodiments described above, the controller 100 is coupled to the electrode(s) of the outer cutting blade via an electrical connector 40A provided on an external surface near the proximal end of the outer cutting blade 10. However, other connection arrangements are possible. For example, the controller 100 could be coupled to the electrode(s) through the hub 15 located within the handpiece 2.

In the embodiment described above, the signal output from rotation sensor 70 is used by controller 100 to determine the position of the inner cutting blade 9 relative to the outer cutting blade 10. Based on the determined relative position, an appropriately-controlled signal is provided by controller 100 to the electrode(s) provided adjacent to the distal end of the outer cutting blade 10. The signal can be sufficient for performing electrical cutting (vaporization) of tissue as described above. In addition, or alternatively, the signal can be appropriate for achieving coagulation of tissue as described above. Because it is only desirable to cut/vaporize tissue that is grasped by the windows 30/40 of the cutting blades 9/10, the vaporization signal preferably is only supplied while tissue is being grasped by the cutting surfaces of the windows 30/40. That is, when the outer cutting window 40 is completely closed due to the rotational position of the inner cutting blade 9, the vaporization signal should not be supplied. Otherwise, other tissue in contact with the distal tip of the outer cutting blade 10 could be undesirably vaporized. In addition, because there generally is no reason to coagulate tissue while the cutting is occurring, the coagulation signal (if it is provided) preferably is provided only while tissue cutting is not occurring (that is, while the cutting window 40 of the outer cutting blade 10 is closed due to the rotational position of the inner cutting blade 9). The coagulation signal also could be supplied during the period when the cutting window 40 begins to open because cutting is not occurring at that time. As noted previously, the coagulation signal can be provided even when the instrument is being used to perform only mechanical cutting (that is, the vaporization signal is not being used in conjunction with the mechanical cutting). In such an embodiment, the coagulation signal preferably is supplied only when the cutting windows 30/40 are not cutting through tissue.

As also noted previously, if electromechanical cutting is being conducted, then it is preferable to rotate the inner cutting blade 9 at a speed slower than what is usually used to perform mechanical cutting. For example, the inner cutting blade can be rotated at less than about 60 rpm (revolutions per minute) if electromechanical cutting is being conducted. The slower rotation speed can be used due to the cutting assistance provided by the vaporization signal. Additionally, the slower rotation speed is preferable because it will make it easier for the surgeon to grasp more tissue with the instrument. The electromechanical action may provide a cleaner, more precise cut of larger "bites" of tissue compared with mechanical cutting. Purely mechanical cutting at higher speeds often chews (multiple rotations required to take a large "bite") tissue, and may be limited to smaller "bites" of tissue due to the relatively small time frame in which the cutting window is open.

In the first described embodiment, magnetic sensor 70 is used to sense the relative positions of the inner and outer cutting blades, and then that sensed information is used by controller 100 to control the signal that is supplied to the electrode(s). Some of the following more simple embodiments directly supply a signal (for example, a coagulation signal) to the electrode based on the relative positions of the inner and outer cutting blades without using a sensor.

In the following embodiments, the electrical signal is provided to the inner cutting blade, and the electrical signal is provided only for performing coagulation. Because the inner and outer cutting blades 9/10 preferably are made from electrically conductive material, supplying the electrical signal to the inner cutting blade 9 will still result in the coagulation energy reaching the tissue after traveling through the distal end of the outer cutting blade 10. That is, the inner and outer cutting blades are in physical and electrical contact with each other at least at their distal ends so that the signal will be conducted from the inner cutting blade to the outer cutting blade.

Figure 10:
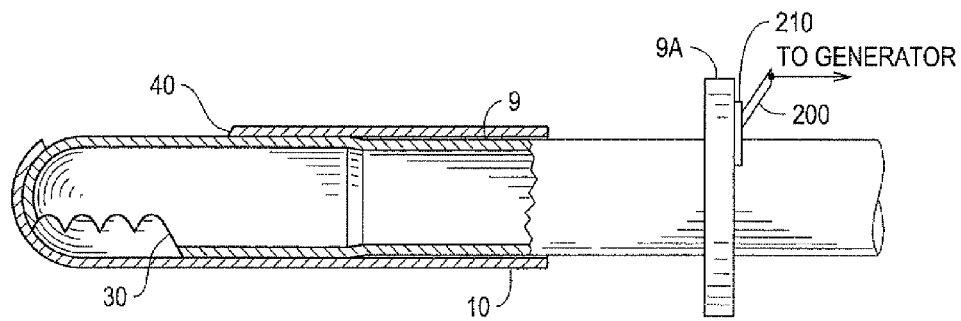
FIG. 10 is a side view of an embodiment in which a leaf spring contacts the drive gear of the inner cutting blade to provide a coagulation signal.
Figure 11:
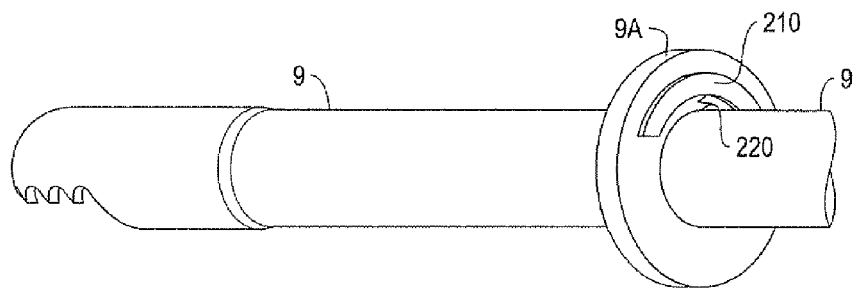
FIG. 11 is a perspective view of the FIG. 10 inner cutting blade.

FIGS. 10 and 11 show an embodiment in which the electrical signal is supplied to the inner cutting blade 9 through a gear 9A that is used to couple the inner cutting blade 9 to a motor that rotates the blade. In FIG. 10, the relative positions of the inner and outer cutting blades 9/10 is such that the inner and outer cutting windows 30/40 are misaligned (that is, the outer cutting window 40 is blocked by the distal end of the inner cutting blade 9). This is one position where it is desirable to provide coagulation energy. A generator supplies the coagulation signal to the handpiece. Inside the handpiece, an electrical leaf spring 200 made from a material such as BeCu is connected to the inner cutting blade 9 (the distal tip of which functions as an electrode) through the gear 9A. In particular, an electrical pad 210 is provided on a side surface of the drive gear 9A. The drive gear 9A is made from a non-conducting material such as, for example, acetal. FIG. 11 shows the electrical pad 210 in more detail. The electrical pad 210 is electrically connected to the inner cutting blade 9 via a conductor 220 such as a wire. As can be appreciated from FIGS. 10 and 11, the pad 210 extends along an arc such that it will remain in contact with the leaf spring 200, and thus receive the coagulation signal, for a portion of each revolution of the cutting blade 9. By precisely controlling the length of the pad 210, the portion of each rotation of the inner cutting blade 9 during which the coagulation signal is supplied to the distal tip of the instrument can be precisely controlled.

Figure 12:
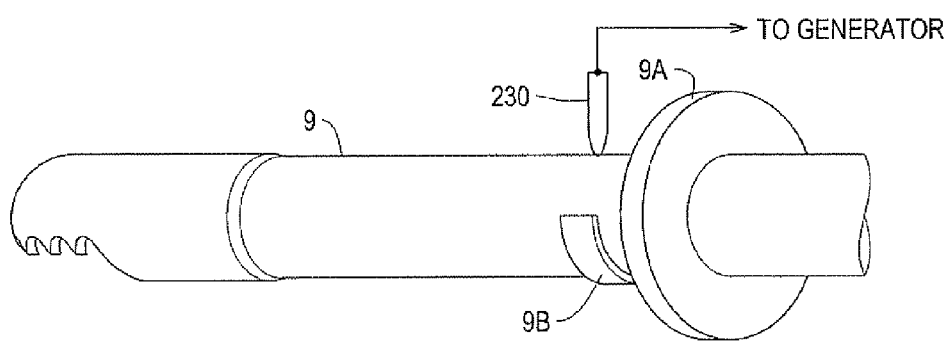
FIG. 12 is a side view of an embodiment in which a leaf spring contacts an outer surface of the inner cutting blade to provide a coagulation signal.
Figure 13:
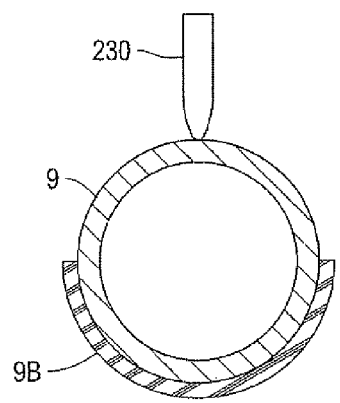
FIG. 13 is a cross-sectional view of the FIG. 12 inner cutting blade.

FIGS. 12 and 13 show another embodiment. In the embodiment of FIGS. 12 and 13, a leaf spring 230, connected to a generator so as to receive the coagulation signal, rides on the outer surface of the inner cutting blade 9. A portion of the outer surface of inner cutting blade 9 is covered by an electrically non-conductive pad 9B. When the leaf spring 230 directly contacts the outer surface of the inner cutting blade 9, the distal tip of the instrument will receive and apply coagulation energy to tissue in contact with the distal tip. When the leaf spring 230 contacts the pad 9B, no coagulation signal is provided to the distal tip of the instrument because the pad 9B is electrically non-conductive and thus insulates the cutting blade 9 from the leaf spring 230. Again, the radial extent of the pad 9B can be precisely controlled to affect the portion of the inner blade 9 rotation during which the coagulation signal will not be supplied to the distal tip of the instrument.

In the embodiments shown in FIGS. 10-13, the orientation of the outer cutting blade 10 relative to the handpiece 2 is fixed and not adjustable. However, as is well known in the art, it is possible to adjust the orientation of the outer cutting blade 10 relative to the handpiece (for example, so that the orientation of the outer cutting window 40 can be adjusted).

If the orientation of the outer cutting blade 10 is adjustable, then information is needed with respect to the orientation of the outer cutting blade 10 (more specifically, of the orientation of the outer cutting window 40) so that the coagulation signal can be provided at the appropriate time (for example, when the cutting windows 30 and 40 are not in alignment). FIGS. 14-16 show embodiments in which information about the orientations of the inner and outer cutting blades 9/10 can be obtained in order to control when the coagulation signal is to be supplied.

In the embodiment of FIGS. 14 and 15, each of the cutting blades 9/10 includes an eccentric cam. In addition, a transducer or sensor such as, for example, a linear variable displacement transducer (LVDT) is provided to interact with each of the cams so as to obtain information about the position of the cutting blade associated with that cam. As shown in FIG. 14, inner cutting blade 9 having gear 9A includes a cam 320. LVDT 340 having a sensor arm which contacts the outer periphery of the cam 320 is used to detect the rotational position of inner cutting blade 9. As the inner cutting blade 9 rotates, the sensor arm of LVDT 340, which is biased toward and against the outer periphery of the cam, will move up and down, thus indicating the rotational position of the inner cutting blade 9. Because the orientation of the cam with respect to the cutting window 30 of the blade 9 is known, the signal will indicate the position of the cutting window 30 (for example, with respect to FIGS. 14 and 15, information can be determined as to whether the cutting window 30 is pointing upward, downward, or to positions therebetween). Outer cutting blade 10 has a similar cam 310 and LVDT 330. Before a cutting operation begins, the rotational position of the outer cutting blade 10 can be adjusted relative to the handpiece 2 (although the blade 10 will not rotate during a cutting operation), and thus the LVDT 330 can be used to determine the position to which outer cutting blade 10 has been adjusted. Thus, the location/orientation of the outer cutting window 40 will be known. Controller 100 receives the signals output from the LVDTs 330 and 340, and can thus determine when the cutting windows 30 and 40 are aligned and misaligned. Accordingly, controller 100 can determine when the coagulation signal should be supplied to the inner cutting blade 9, which is electrically coupled to a generator via the controller 100.

FIG. 16 shows a different type of transducer system. In FIG. 16, the inner cutting blade 9 is provided with an outer ring 400 having electrically conductive portions 410 and electrically non-conductive portions 420. Three electrically conductive pins 450A, 450B and 450C are biased against the ring 400. When the pins come into contact with one of the electrically conductive portions 410, that condition can be detected. The positions of the pins 450A-450C and of the electrically conductive portions 410 can be chosen such that information about the position of the cutting window 30 on cutting blade 9 can be known. More or less than three pins can be provided as needed. A similar arrangement can be provided for the outer cutting blade 10 if the outer cutting blade is adjustable relative to the handpiece.

Although the embodiments of FIGS. 10-16 were described with respect to applying a coagulation signal, the embodiments could be used to apply a vaporization signal or to apply both a coagulation signal and a vaporization signal. For example, referring to the embodiment of FIGS. 10 and 11, an electrical pad similar to electrical pad 210 can be provided in alignment with the cutting window 30 (rather than out of alignment with the cutting window 30 as is pad 210) and an additional leaf spring similar to leaf spring 200 but coupled to a vaporization signal generator can be provided to alternately contact the electrical pad. If both vaporization and coagulation signals are to be applied, the electrical pad for vaporization and the electrical pad 210 for coagulation can be provided at different radial positions on the gear 9A.

Figure 17:
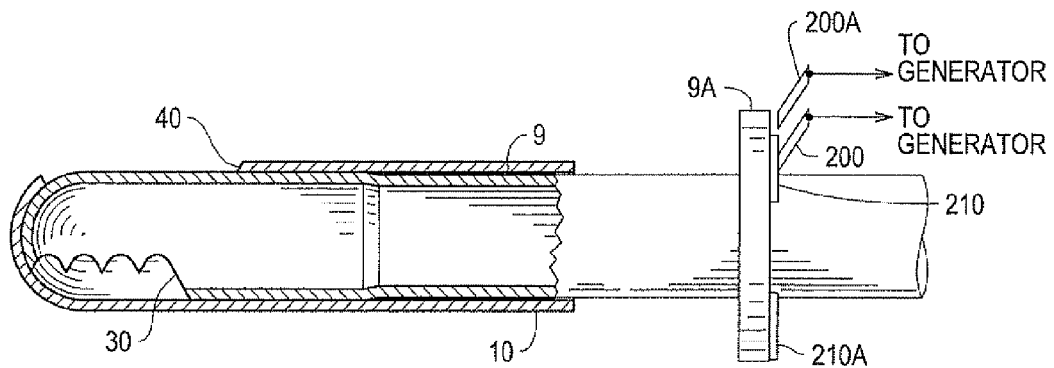
FIGS. 17 and 18 are similar to FIGS. 10 and 11, but show an embodiment in which both coagulation energy and vaporization energy are selectively applied.
Figure 18:
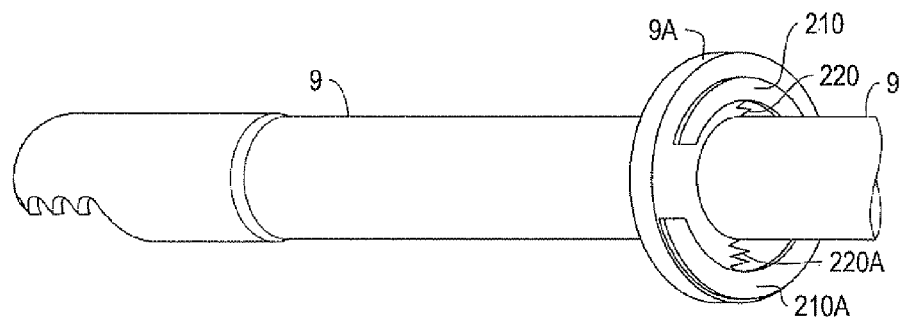

FIGS. 17 and 18 show a modified version of the embodiment of FIGS. 10 and 11 in which coagulation and vaporization signals are selectively applied. A generator supplies the coagulation signal and the vaporization signal to the handpiece. Inside the handpiece, a first electrical leaf spring 200 made from a material such as BeCu is connected to the inner cutting blade 9 (the distal tip of which functions as an electrode) through the gear 9A. In particular, a first electrical pad 210 is provided on a side surface of the drive gear 9A. The drive gear 9A is made from a non-conducting material such as, for example, acetal. FIG. 18 shows the first electrical pad 210 in more detail. The first electrical pad 210 is electrically connected to the inner cutting blade 9 via a first conductor 220 such as a wire. As can be appreciated from FIGS. 17 and 18, the first pad 210 extends along an arc such that it will remain in contact with the first leaf spring 200, and thus receive the coagulation signal, for a portion of each revolution of the cutting blade 9. By precisely controlling the length of the first pad 210, the portion of each rotation of the inner cutting blade 9 during which the coagulation signal is supplied to the distal tip of the instrument can be precisely controlled. A second electrical pad 210A is provided on the side surface of the drive gear 9A. The second pad 210A can be provided on the same side of the drive gear 9A as the first pad 210, or on the opposite side of the gear 9A. FIG. 18 shows the second electrical pad 210A in more detail. The second electrical pad 210A is electrically connected to the inner cutting blade 9 via a second conductor 220A such as a wire. As can be appreciated from FIGS. 17 and 18, the second pad 210A extends along an arc such that it will remain in contact with a second leaf spring 200A, and thus receive the vaporization signal, for a portion of each revolution of the cutting blade 9. By precisely controlling the length of the second pad 210A, the portion of each rotation of the inner cutting blade 9 during which the vaporization signal is supplied to the distal tip of the instrument can be precisely controlled. The second pad 210A is located radially farther away from the center of the gear 9A than is the first pad 210 so that second pad 210A will only contact second leaf spring 200A, and so that first pad 210 will only contact first leaf spring 200.

Figure 19:
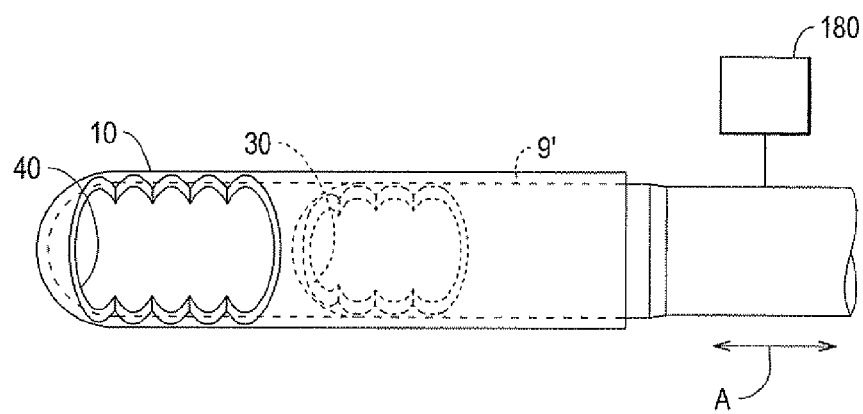
FIG. 19 is a schematic view of a surgical cutting instrument in which the inner cutting blade reciprocates.

As noted previously, the inner cutting blade 9 can reciprocate along the longitudinal axis LA of the instrument instead of rotating about the longitudinal axis. In addition, the inner cutting blade 9 can reciprocate and rotate. FIG. 19 shows an example of an inner cutting blade that reciprocates and rotates.

FIG. 19 is a schematic drawing of a variation of any of the previously described embodiments in which the inner cutting blade 9' (having cutting window 30) reciprocates in the direction of arrow A in the longitudinal axis direction of the surgical instrument. A drive mechanism 180 drives the inner cutting blade in the longitudinal axis direction. Any well known type of drive mechanism can be used. For example, the longitudinal reciprocation drive mechanism disclosed in U.S. Pat. No. 5,106,364, the disclosure of which is incorporated herein by reference in its entirety, can be used. The inner cutting blade 9/9' also could be rotated and reciprocated.

Figure 20:
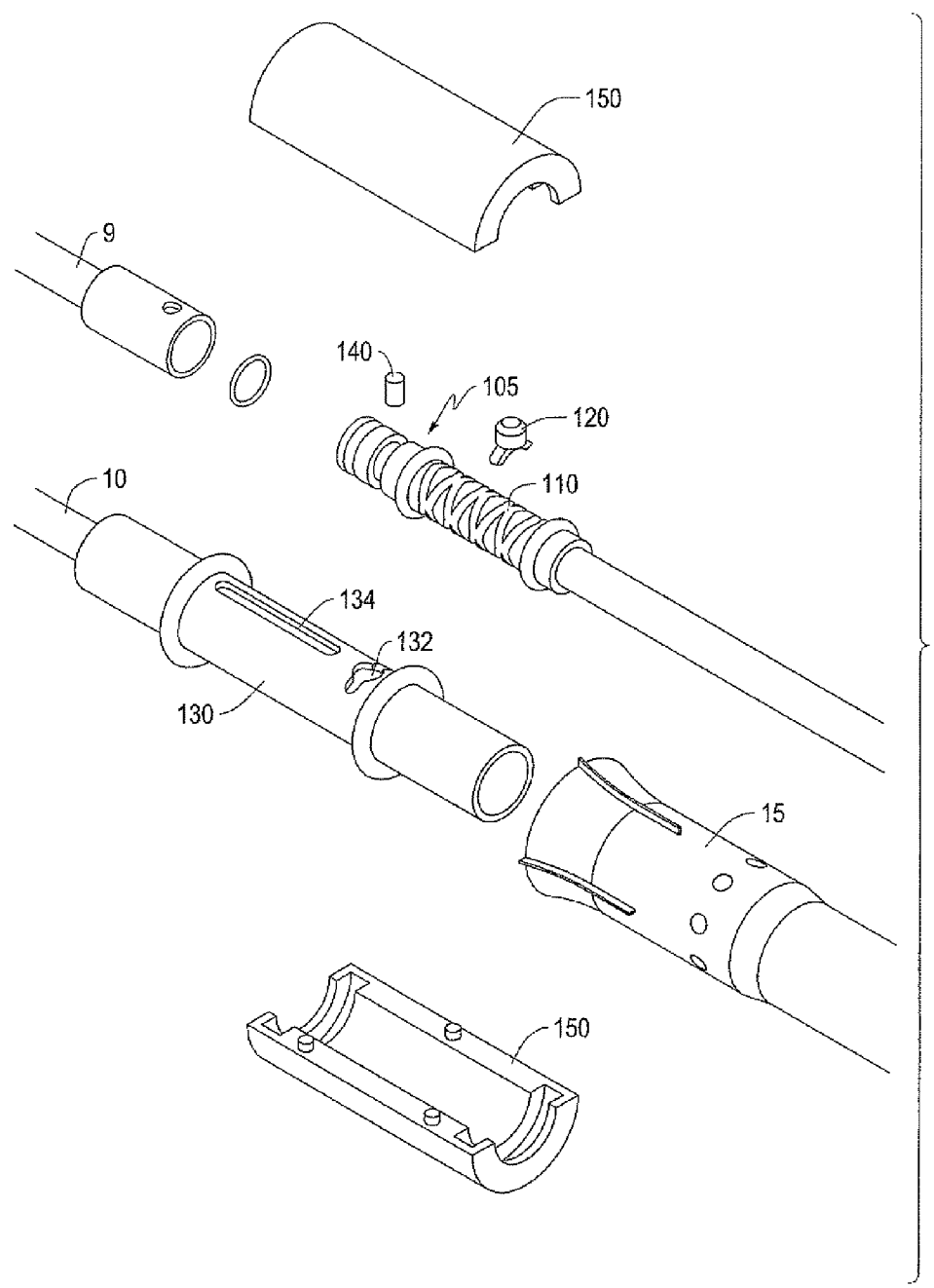
FIGS. 20 and 21 are perspective views of an embodiment in which the inner cutting blade rotates (about the longitudinal axis of the device) and reciprocates (along the longitudinal axis of the device).
Figure 21:
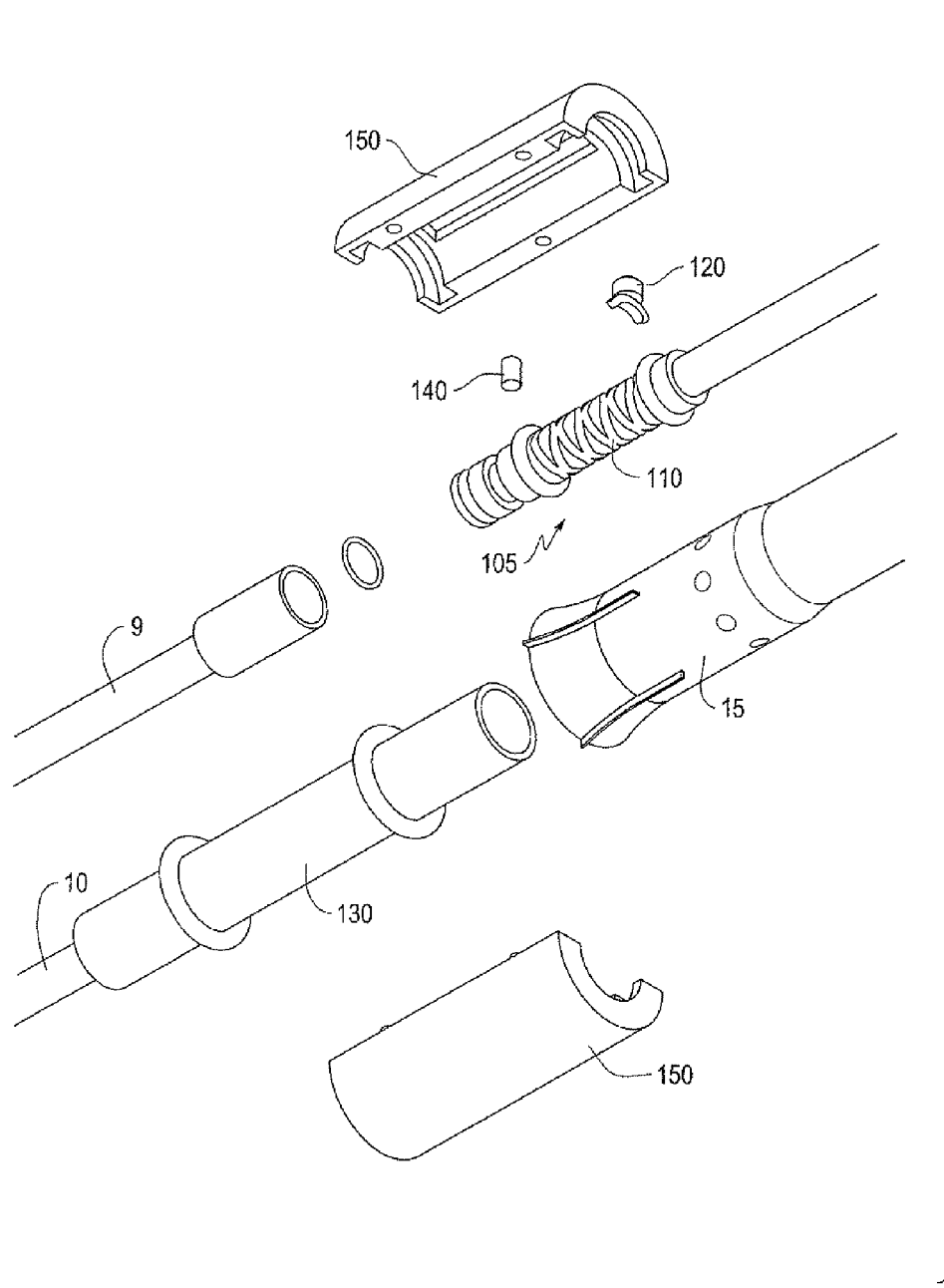

FIGS. 20 and 21 are perspective, exploded views of a drive mechanism that rotates and reciprocates the inner cutting blade 9. The reciprocal gear mechanism is based on a levelwind gear mechanism commonly seen in various consumer products such as fishing reels and hose take-up reels. The reciprocal gear has a single continuous helical groove, or track, 110 that winds in both right-hand and left-hand directions along the outer surface of the gear body 105. An inner hub (not shown) is rigidly affixed to the proximal portion of the inner drive member and transfers the input rotational motion from the powered handpiece. A proximal portion of the inner drive member is rigidly fixed to the proximal end of the gear. A follower pin 120 is mounted in a stationary outer tube assembly 130 and extends through hole 132 in that assembly, and causes the gear 105 to reciprocate axially as it is driven by the handpiece. The pin 120 is allowed to rotate on its axis at the ends of the stroke, as the track 110 changes direction and rotates the opposite way. The outer tube assembly 130 and pin 120 are rigidly affixed to an outer hub 150, all of which remain stationary while the device is in use. The pin 120 is constructed with a "wishbone" shape, which allows the leading edge of the pin to be guided into the correct track 110 by the trailing edge of the pin. Because the pin 120 straddles the gear 105, either the leading or trailing portion of the pin 120 is always engaged in the groove of the gear, even where the right-hand and left-hand portions of the track cross one another.

On the distal end of the gear body 105, the distal portion of the inner cutting blade 9 is axially constrained (but not necessarily rotationally constrained) to the gear such that the linear motion of the gear 105 is translated to the distal section of the inner cutting blade 9. If the inner cutting blade 9 both rotates and reciprocates, the cutting blade 9 is fixed to the gear 105 with respect to both rotation and translation. If the inner cutting blade 9 only reciprocates (but remains in plane with the outer cutting blade 10), the cutting blade 9 is allowed to rotate with respect to the gear 105. However, the distal section of the inner cutting blade 9 is pinned or otherwise affixed in plane to the outer cutting blade 10 to allow reciprocation, but not rotation. For example, a guide pin 140 extends through a hole in the cutting blade 9 and rides in a channel on an outer surface of the gear 105 near the distal end of the gear 105 so that the cutting blade 9 is axially fixed to the gear 105, but can rotate with respect to the gear 105. The guide pin 140 also passes through a slot 134 in the outer tube assembly 130 so that the inner and outer blades 9 and 10 remain properly aligned (if the inner blade 9 only reciprocates). The guide pin 140 and slot would be omitted if the inner blade 9 also rotated with respect to the outer blade 10.

The construction of the remainder of the device (for example, the distal ends of the inner and outer cutting blades and the vacuum and liquid supply passages) can be similar to what was described above for the previous embodiments. The stroke of the inner cutting blade assembly is determined by the axial length of the groove. The gear relationship between rotation and reciprocation is based on the number of turns in the gear to complete the length of the track (stroke) on the gear. For example, if the gear track makes three turns to complete the retrograde stroke and three turns to complete the prograde stroke, and the input speed from the handpiece is 12,000 rpm, then, for a device that rotates and reciprocates, the distal cutting tip will rotate at 12,000 rpm and reciprocate at 2,000 rpm (three turns retrograde and three turns prograde equals six rotations to complete one full reciprocal stroke). In general, a longer stroke allows a greater motion ratio between rotation and reciprocation.

In the illustrated embodiment, the inner and outer cutting blades 9 and 10 are straight. However, the surgical instrument 8 can have one or more bends in it such that it is not straight. In such an arrangement, the inner cutting blade 9 would be flexible. Flexible hollow cutting blades are known and used with curved cutting instruments. See, for example, U.S. Pat. No. 4,646,738, the disclosure of which is incorporated herein by reference in its entirety, and see, for example, U.S. Pat. No. 5,707,350, the disclosure of which is incorporated herein by reference in its entirety.

The illustrated exemplary embodiments of the surgical tool as set forth above are intended to be illustrative and not limiting. Various changes may be made without departing from the spirit and scope of the invention.

What is claimed is:

1. A surgical cutting instrument comprising:
   a first cutting blade having a tubular body with a distal end and a proximal end, a cutting window that is sideward-facing disposed at the distal end and including a cutting edge;
   a second cutting blade movably disposed inside the first cutting blade and having a distal cutting portion that, together with the cutting edge of the cutting window, cuts tissue by moving within the first cutting blade;
   at least one first electrode located adjacent to at least the cutting edge at the distal end of the first cutting blade; and
   control circuitry configured to control an electrical power signal supplied to the at least one first electrode, the control circuitry varying the electrical power signal based on a position of the second cutting blade relative to the first cutting blade, a rotating speed of the second cutting blade, or both.

2. The surgical cutting instrument of claim 1, wherein:
   the second cutting blade moves between a first position at which the tissue to be cut is permitted to enter the cutting window, and a second position at which the tissue has been cut by the cutting window, and
   the control circuitry supplies (i) a first electrical power signal at least part of the time while the second cutting blade is in the first position, and (ii) a second electrical power signal, which is different from the first electrical power signal, at least part of the time while the second cutting blade is in the second position.

3. The surgical cutting instrument of claim 2, wherein the first electrical power signal causes the tissue to be cut.

4. The surgical cutting instrument of claim 3, wherein the second electrical power signal causes the tissue to be coagulated.

5. The surgical cutting instrument of claim 3, wherein the second electrical power signal is a zero power signal.

6. The surgical cutting instrument of claim 2, wherein the second electrical power signal causes the tissue to be coagulated.

7. The surgical cutting instrument of claim 6, wherein the first electrical power signal is a zero power signal.

8. The surgical cutting instrument of claim 1, wherein the electrical power signal supplied by the control circuitry is a monopolar signal.

9. The surgical cutting instrument of claim 1, further comprising:
   an insulation layer disposed over at least a portion of the distal end of the first cutting blade; and
   at least one second electrode located over at least a portion of the insulation layer and electrically coupled to the control circuitry,
   wherein the electrical power signal supplied by the control circuitry is a bipolar signal.

10. The surgical cutting instrument of claim 1, wherein suction is applied through the cutting window at the distal end of the first cutting blade.

11. The surgical cutting instrument of claim 1, wherein the second cutting blade rotates about a longitudinal axis of the surgical cutting instrument.

12. The surgical cutting instrument of claim 1, wherein the second cutting blade reciprocates in a longitudinal direction of the surgical cutting instrument.

13. The surgical cutting instrument of claim 1, wherein the control circuitry includes:
    a sensor that senses a position of the second cutting blade relative to the first cutting blade, a rotational speed of the second cutting blade, or both, and
    a processor that varies the electrical power signal based on the sensed position of the second cutting blade relative to the first cutting blade.

14. The surgical cutting instrument of claim 1, wherein the control circuitry includes:
    at least one moving electrical contact coupled to the second cutting blade, and
    at least one fixed contact that intermittently contacts the at least one moving electrical contact as the second cutting blade moves.

15. The surgical cutting instrument of claim 1, wherein:
    the second cutting blade moves between a first position at which at least a part of the distal cutting portion faces the cutting window, and a second position at which the distal cutting portion does not face the cutting window, and
    the control circuitry supplies (i) a first electrical power signal at least part of the time while the second cutting blade is in the first position, and (ii) a second electrical power signal, which is different from the first electrical power signal, at least part of the time while the second cutting blade is in the second position.

16. A surgical cutting instrument comprising:
    a first cutting blade having a tubular body with a proximal end and a distal end, a cutting window disposed at a side of the first cutting blade near the distal end;
    a second cutting blade having a tubular body with a proximal end and a distal end, a cutting window disposed at a side of the second cutting blade near the distal end, the second cutting blade rotatably disposed inside of the first cutting blade such that the surgical cutting instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade;
    at least one first electrode located adjacent to at least the cutting window at the distal end of the first cutting blade;
    a sensor that senses a rotational position of the second cutting blade relative to the first cutting blade; and
    a processor that controls an electrical power signal supplied to the at least one first electrode at least partially based on the sensed rotational position of the second cutting blade relative to the first cutting blade, the processor supplying (i) a first electrical power signal at least part of the time while the cutting windows of the first and second cutting blades are aligned with each other, and (ii) a second electrical power signal, which is different from the first electrical power signal, at least part of the time while the cutting windows of the first and second cutting blades are not aligned with each other.

17. A surgical cutting instrument comprising:
    a first cutting blade having a tubular body with a proximal end and a distal end, a cutting window disposed at a side of the first cutting blade near the distal end;
    a second cutting blade having a tubular body with a proximal end and a distal end, a cutting window disposed at a side of the second cutting blade near the distal end, the second cutting blade rotatably disposed inside of the first cutting blade such that the surgical cutting instrument cuts tissue by rotating the second cutting blade within the first cutting blade while a vacuum is applied through an internal bore of the second cutting blade to draw the tissue into the cutting windows of the first and second cutting blades and sever the tissue by rotation of the second cutting blade;
    at least one first electrode located adjacent to at least the cutting window at the distal end of the first cutting blade; and
    control circuitry coupled to at least the second cutting blade and that supplies an electrical power signal to the at least one first electrode, the control circuitry supplying (i) a first electrical power signal at least part of the time while the cutting windows of the first and second cutting blades are aligned with each other, and (ii) a second electrical power signal, which is different from the first electrical power signal, at least part of the time while the cutting windows of the first and second cutting blades are not aligned with each other.

* * * * *